United States Patent [19]
Bradfield

[11] Patent Number: 5,879,552
[45] Date of Patent: Mar. 9, 1999

[54] METHOD AND APPARATUS FOR A SELF-PURIFYING FILTER SYSTEM

[76] Inventor: Michael T. Bradfield, 10210 S. Golden Willow Dr., Sandy, Utah 84070

[21] Appl. No.: 904,110

[22] Filed: Jul. 31, 1997

Related U.S. Application Data

[60] Provisional application No. 60/028,383 Oct. 15, 1996.

[51] Int. Cl.[6] .......................... B01D 29/66; B01D 29/68; B01D 36/00; A61C 17/06
[52] U.S. Cl. .......................... 210/411; 210/108; 210/111; 210/113; 210/406; 210/304; 210/312; 210/313; 210/258; 210/259; 210/123; 210/436; 210/512.1; 55/337; 55/432; 96/233; 433/92; 433/97
[58] Field of Search ...................................... 210/108, 111, 210/406, 411, 416.1, 304, 312, 313, 258, 259, 123, 436, 512.1, 113; 55/337, 431, 432, 303; 96/233; 433/92, 97

[56] References Cited

U.S. PATENT DOCUMENTS

| | | |
|---|---|---|
| 2,784,717 | 3/1957 | Thompson . |
| 2,821,021 | 1/1958 | Winter . |
| 4,164,384 | 8/1979 | Hertell ...................................... 418/47 |
| 4,385,891 | 5/1983 | Ligotti . |
| 4,386,910 | 6/1983 | Cattani . |
| 4,589,442 | 5/1986 | Ernryd . |
| 4,963,094 | 10/1990 | Meyer . |
| 5,080,697 | 1/1992 | Finke .......................................... 55/97 |
| 5,131,825 | 7/1992 | Bachmann et al. .......................... 418/1 |
| 5,141,639 | 8/1992 | Kraus et al. ............................. 210/321 |
| 5,217,357 | 6/1993 | Welch ....................................... 418/46 |
| 5,242,588 | 9/1993 | Reese ...................................... 210/232 |
| 5,282,744 | 2/1994 | Meyer . |
| 5,330,641 | 7/1994 | Cattani . |
| 5,354,468 | 10/1994 | Richards . |
| 5,571,412 | 11/1996 | Nerli . |
| 5,577,910 | 11/1996 | Holland ..................................... 433/92 |
| 5,795,159 | 8/1998 | Ralls . |

*Primary Examiner*—Thomas M. Lithgow
*Attorney, Agent, or Firm*—Workman, Nydegger & Seeley

[57] ABSTRACT

A self-purifying filter apparatus comprising (1) a filter having a first surface and a second surface; (2) flow control means, such as a vacuum pump, for causing a stream of fluid interspersed with solid particulates to pass from the first surface to the second surface through the filter, thereby removing some of the solid particulates from the first stream of fluid and depositing them on the first surface; and (3) a purging device, such as a small reservoir of water (potentially formed, in part, by water previously filtered by the filter), for causing a second stream of fluid to pass from the second surface to the first surface through the filter without substantially changing the position of the filter, thereby rinsing and removing from the first surface at least some of the solid particulates that were deposited there.

7 Claims, 4 Drawing Sheets

METHOD AND APPARATUS FOR A SELF-PURIFYING FILTER SYSTEM

BACKGROUND OF THE INVENTION

Related Applications

This application claims the benefit of the filing date of copending U.S. provisional application Ser. No. 60/028,383, filed Oct. 15, 1996.

Field of the Invention

The present invention relates generally to filters used to prevent solid particulates that are sucked into a vacuum line from harming the vacuum pump. More particularly, the present invention relates to a self-purifying filter apparatus for use with a vacuum pump, where solid particulates are filtered from a liquid or fluid in a vacuum line, and which automatically removes any solid particulates that have been deposited on the filter.

Related Technology

Filters are often used to remove particulates from a vacuum line so as to protect the vacuum pump from damage as the particles pass through the pump. When a filter is used, however, particles and other debris become deposited on one surface of the filter, and after a sufficient accumulation, neither air nor liquid can pass through the filter as required.

Three main solutions have been offered for this problem. First, some filters are made to be removable, so that a person may remove it from its position between a vacuum line and the vacuum pump, clean it, and reinstall it in its proper position.

Another alternative has been to use disposable filters so that when a filter becomes clogged, a person can turn off the vacuum pump, remove the filter, and replace it with a new one.

A third alternative has been to make the filter neither removable nor disposable, but simply accessible so that a person can access the filter in order to clean it.

However, all three of these alternatives suffer from serious disadvantages. All three alternatives require a person to dedicate time to either cleaning a filter or removing and reinstalling a new one. Furthermore, the process of cleaning a filter, depending on what is deposited on it, can be dirty, unhealthy, or even toxic.

In a dentist's office, where wet-style vacuum pumps are routinely used for everyday activities, many of these problems are presented. A vacuum pump allows a dentist or a hygienist to remove excessive saliva from a person's mouth, to remove solid particulates produced by cleaning or drilling, and to remove other items from a patient's mouth primarily as a mixture of water and solid particulates. Conventional vacuum pumps used in a dentist's office employ a removable filter which must be cleaned periodically. The removal of particulates that become deposited on a dentist's office filter can present serious health hazards and is extremely unpleasant. In addition, vacuum pumps such as these are usually located in a remote location. Consequently, the person who is assigned to clean the filter must struggle to gain access to it in order to clean it.

More sophisticated vacuum pumps have a system which monitors the difference in pressure on either side of the filter and illuminates an auto-check light in the dentist's office when the pressure difference becomes too great. In theory, this provides notice to those in the office that the filter needs to be cleaned. However, in practice, if two or more dentists or hygienists are using the same vacuum pump, the auto-check light is not reliable. Because the auto-check light is often not calibrated for use by several persons, such use causes the light to be illuminated even when the filter does not need to be cleaned, thus defeating its purpose. Thus, it can be seen that what is needed in the art are methods and devices that overcome the difficulties associated with removing and/or cleaning conventional filters.

BRIEF SUMMARY AND OBJECTS OF THE INVENTION

The present invention relates to methods and apparati for automatically cleaning a filter. It is an object of the invention to allow cleaning of a filter without exposing a person to dirty, unhealthy, or toxic deposits. It is a further object of the invention to provide methods and devices for automatically cleaning a filter, so that a person does not need to dedicate time to do so. It is also an object of the invention to provide methods and devices for reliably ensuring that a filter is cleaned when it needs to be. It is a further object of the invention to provide methods and devices for implementing such improvements with existing vacuum pumps and filters with little reconfiguration and at an affordable price.

The present invention overcomes the difficulties presented by the prior art by providing a self-purifying filter for wet-style vacuum systems that has no moving parts, and requires no water line hookups nor electrical connections. The device can be easily installed for use with a conventional vacuum pump or embodied within such a vacuum pump. The self-purifying filter may also be adapted for use with dry-style vacuum systems.

The device comprises a vacuum chamber with a filtered chamber disposed within it, the only access from the vacuum chamber into the filtered chamber being through an aperture that is completely covered by a filter. A vacuum line access port provides access to the interior of the filtered chamber and is connected with the vacuum line of a vacuum pump, creating low-pressure within both the filtered chamber and the vacuum chamber. A mixture inlet port allows access to the vacuum chamber, providing a passage through which a mixture of liquid, air, and solid particulates is sucked by virtue of the low-pressure created in the vacuum chamber and in the filtered chamber by the vacuum pump. Some of the heavier solid particulates fall to the floor of the vacuum chamber, and others are filtered from the liquid/air mixture as it passes through the filter into the filtered chamber and out the vacuum line access port. In addition, by offsetting the mixture inlet port from the center of the vacuum chamber, a vortex effect is created which aids in the downward movement of particulates. A valve in the floor of the vacuum chamber allows particulates that have accumulated to exit through a drain when a certain amount of particulates have accumulated or upon the vacuum pump's being shut off.

The most significant feature of the present invention is that when the vacuum pump is shut off, a stream of liquid is caused to pass from within the filtered chamber through the filter, thereby rinsing from the filter any particulates deposited on the filter, and causing them to wash through the valve in the floor of the vacuum chamber and into the drain. The stream of liquid is preferably produced by the release of a small reservoir of water held outside the vacuum chamber and allowed to flow into the filtered chamber by way of a valved aperture. Significantly, the small reservoir of water may be composed of (1) water that has already passed through the filter and filtered chamber and/or (2) water used by the vacuum pump itself as a coolant and a sealant, both of which exit through the vacuum pump's exhaust line. In addition, the required valves can be purely mechanical. In this way, the device does not require additional water line hookups or electrical connections to operate. This provides a significant advantage by allowing the self-purifying filter to be installed without significant reconfiguration or reconstruction of a vacuum pump or an office area.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENT

Figure 1:
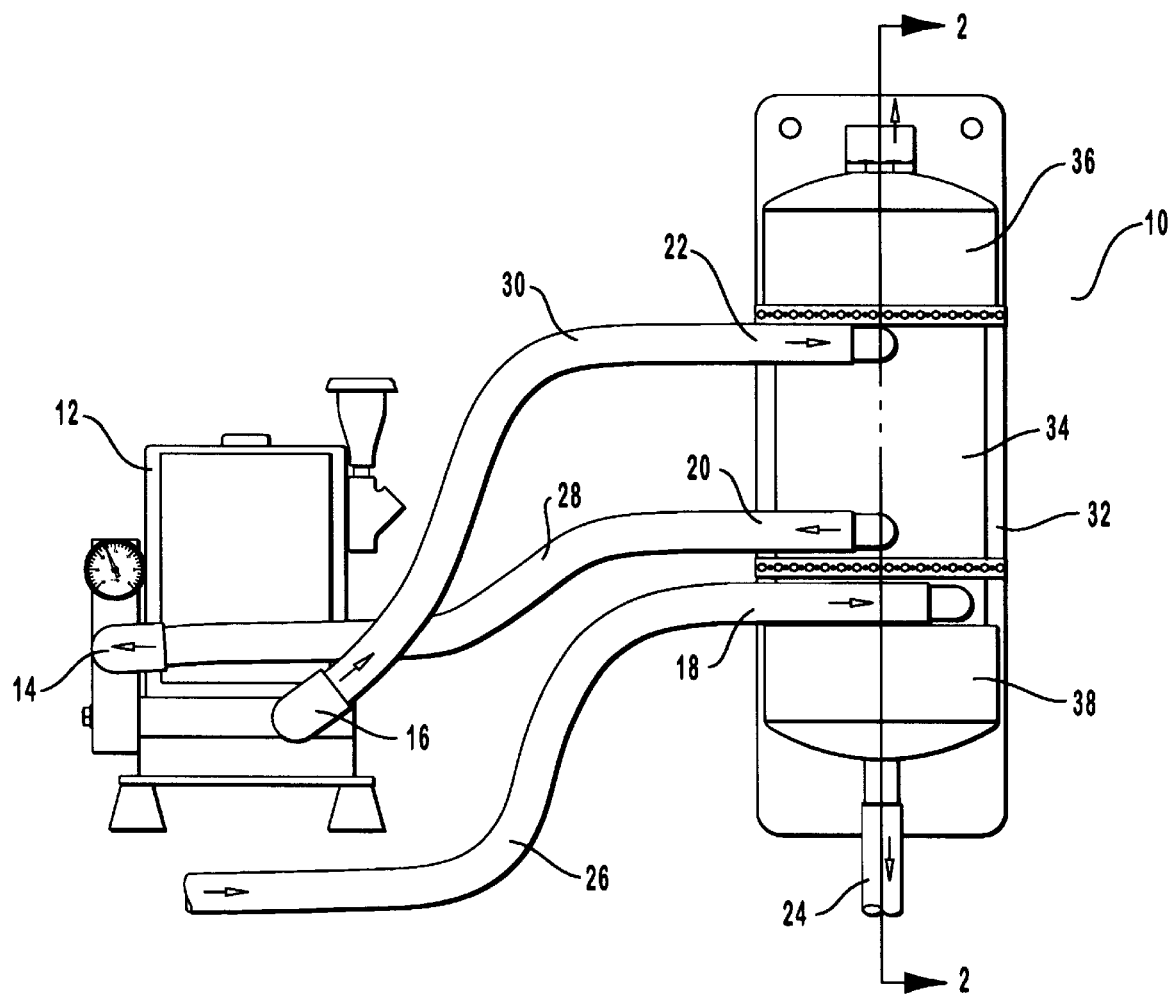
FIG. 1 is a perspective view of the preferred embodiment of a self-purifying filter assembly in working connection with a wet-style vacuum pump.

A self-purifying filter assembly 10 is depicted in FIG. 1 in operation with a conventional wet-style vacuum pump 12, as used in a dentist's office. As illustrated, vacuum pump 12 comprises a vacuum line port 14 and an exhaust line port 16. Self-purifying filter assembly 10 includes a mixture inlet port 18, a vacuum line access port 20, a reservoir input port 22, and a drain tube 24. A mixture inlet hose 26 is connected to mixture inlet port 18, a vacuum line hose 28 connects vacuum line access port 20 to vacuum line port 14, and an exhaust line hose 30 connects exhaust line port 16 to reservoir input port 22. When a flow control means such as vacuum pump 12 is in operation, low pressure is created in vacuum line hose 28 and within self-purifying filter assembly 10, as will be discussed in more detail below. This, in turn, causes a mixture of water, air, and solid particulates originating from a patient's mouth or other source to flow through mixture inlet hose 26, into self-purifying filter assembly 10 via mixture inlet port 18. Inside self-purifying filter assembly 10, the mixture is filtered through a filter 68 (shown in FIG. 2) and passes out of self-purifying filter assembly 10 via vacuum line access port 20, through vacuum line hose 28, and into vacuum pump 12 via vacuum line port 14. The filtered mixture then is combined with water used as a coolant and sealant by vacuum pump 12 and passes out of vacuum pump 12 via exhaust line port 16, through exhaust line hose 30, and into self-purifying filter assembly 10 via reservoir input port 22. As more fully described below, self-purifying filter assembly 10 stores a small portion of this water as a small reservoir 86, shown in FIG. 2, (the remainder exiting through drain 24), and when vacuum pump 12 is turned off, reservoir 86 is used to rinse material deposited on filter 68 out through drain 24. Drain 24 is preferably connected to a sewer or other appropriate line.

As depicted in FIG. 1, a housing 32 encloses a preferred embodiment of the present invention. Housing 32 comprises an outer tube 34, a top end cap 36, and a bottom end cap 38.

Figure 2:
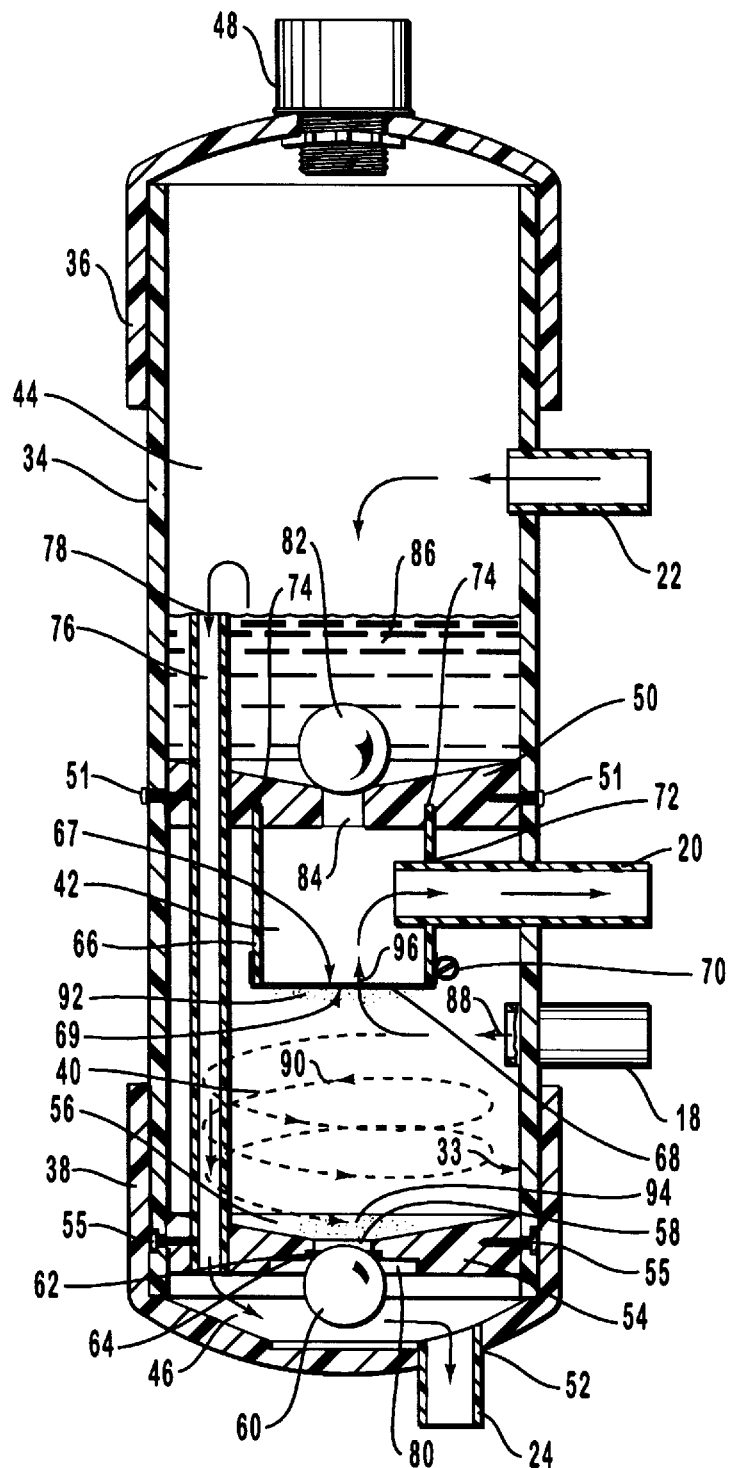
FIG. 2 is a cross-sectional view of the self-purifying filter assembly shown in FIG. 1 and specifically reveals the flow of solid particulates and fluid, as well as the position of a reservoir, while the self-purifying filter is operating to filter solid particulates from an incoming mixture of solid particulates and fluid.

As depicted in FIG. 2, contained within outer tube 34 are a vacuum chamber 40, a filtered chamber 42, a reservoir chamber 44, and a drain chamber 46.

In a preferred embodiment illustrated in FIG. 2, outer tube 34 is substantially cylindrical and is fabricated from roughly an 18-inch length of 6-inch diameter PVC pipe. Top end cap 36 is sized to fit over the top end of outer tube 34 and contains an air vent 48 disposed at the apex of top end cap 36. Top end cap 36 is constructed of a 6-inch diameter Schedule 40 PVC end cap. When top end cap 36 is placed on outer tube 34, the limits of reservoir chamber 44 are defined by top end cap 36, outer tube 34, and a top baffle 50.

Bottom end cap 38 is similarly constructed from a 6-inch diameter Schedule 40 PVC end cap. Bored within bottom end cap 38 is a drain aperture 52, in which drain tube 24 has been inserted. Drain tube 24 comprises a ¾-inch diameter Schedule 40 PVC pipe and is offset from the longitudinal axis of outer tube 34. When bottom end cap 38 is placed on outer tube 34, the limits of drain chamber 46 are defined by a bottom baffle 54, outer tube 34, and bottom end cap 38.

Figure 4:
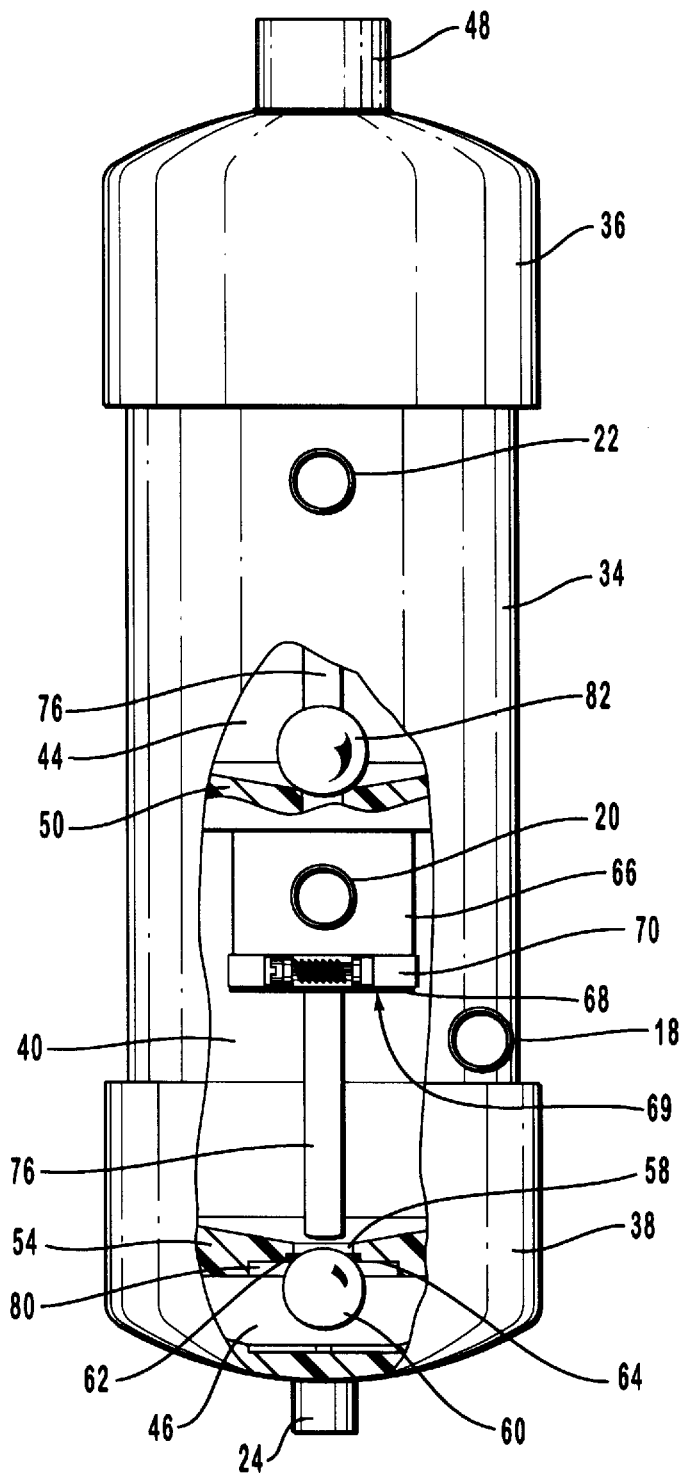
FIG. 4 is a cut-away perspective view of a self-purifying filter assembly like that shown in FIG. 1.

The limits of vacuum chamber 40 are defined by top baffle 50, outer tube 34, and bottom baffle 54. As described above, a mixture of fluid and solid particulates 88 (usually water, air, and solid particulates) enters self-purifying filter assembly 10 via mixture inlet port 18; more specifically, mixture 88 enters vacuum chamber 40. Mixture inlet port 18 is positioned, as shown best in FIG. 4, off center, or such that its longitudinal axis is tangent to an imaginary cylinder disposed concentrically within vacuum chamber 40. Moreover, the cross sectional area of mixture inlet port 18 or mixture inlet hose 26 is relatively small compared to that of vacuum chamber 40. Thus, when under the influence of the low-pressure created by vacuum pump 12, mixture 88 enters vacuum chamber 40 via mixture inlet port 18, and the velocity of mixture 88 rapidly decreases. The heaviest of the solid particulates 94 in mixture 88 are drawn, under the influence of gravitational forces, into a vortex path 90 substantially along an inner surface 33 of outer tube 34 and downward onto bottom baffle 54, where solid particulates 94 tend to slide down a sloped top surface 56 of bottom baffle 54 toward a waste exit aperture 58. However, waste exit aperture 58 is valved shut by a ball 60 pulled upward by the low pressure within vacuum chamber 40 to seal against an O-ring 62 and O-ring 62 is placed concentrically below waste exit aperture 58 within a first recess 64 formed in bottom baffle 54. Both bottom baffle 54 and top baffle 50 are each held in place within outer tube 34 by two sets of screws 55, 55 and 51, 51 respectively.

Meanwhile, the remainder of mixture 88 is drawn through filtered chamber 42 and out of self-purifying filter assembly 10 via vacuum line access port 20, substantially following a path 96. In the preferred embodiment, vacuum line access port 20 is an enclosed tube open only at its ends, forcing any flow generated as a result of vacuum pump 12 to pass through filtered chamber 42 before reaching vacuum pump 12. The limits of filtered chamber 42 are defined by top baffle 50, an inner tube 66, and a filter 68. Inner tube 66 is substantially cylindrical and is constructed of 2.5-inch Schedule 40 PVC pipe. Filter 68 comprises a screen or other suitable filtering material and is secured to an end of inner tube 66 by means of a hose clamp 70. Filter 68 comprises an upper surface 67 and a lower surface 69. Inner tube 66 also contains in its side wall an aperture 72 through which vacuum line access port 20 extends. Inner tube 66 is received into a circular slot 74 formed in the bottom of top baffle 50. Thus, when vacuum pump 12 is in operation, and mixture 88 enters vacuum chamber 40 via mixture inlet port 18, some of the particulates in mixture 88 are drawn downward to bottom baffle 54, substantially following vortex path 90, and the remainder of mixture 88 is drawn through filter 68, into filtered chamber 42, and out through vacuum line access port 20, substantially following path 96. Most, if not all, of the particulates remaining in the fluid drawn upward along path 96 through filter 68 are deposited as deposits 92 on lower surface 69 of filter 68.

At some point, the weight of the accumulating particulates 94 resting on top surface 56 of bottom baffle 54, and more particularly on ball 60, becomes greater than the upward force exerted by virtue of the low pressure within vacuum chamber 40. Thus ball 60 moves downward, allowing particles 94 to exit vacuum chamber 40 through waste exit aperture 58, into drain chamber 46, and out drain aperture 52 into drain tube 54. The movement of these particulates is facilitated by a relatively steady stream of water from a reservoir overflow tube 76, which extends from reservoir chamber 44 to drain chamber 46, unaccessible from top baffle 50, vacuum chamber 40, and bottom baffle 54, through which it extends. Reservoir overflow tube 76 is positioned so as to allow water to drain from reservoir chamber 44 as long as the water level remains at or above an upper end 78 of reservoir overflow tube 76. As will be described later, most of the water flowing through reservoir overflow tube 76 is water used by vacuum pump 12 as a coolant and sealant, in conventional vacuum pumps, such water is used and exhausted at a rate of approximately ½ to 1 gallon per minute.

It should be noted that the radial movement of ball 60 is constrained by the edges of a second recess 80, formed within bottom baffle 54. Second recess 80 is substantially cylindrical, like first recess 64 and is located substantially concentrically with respect to but having a larger diameter than first recess 64. As described above, ball 60 is forced downward when the weight of accumulated particulates 94 reaches a certain amount. As soon as the force exerted on ball 60 by downward moving particulates is once again exceeded by the upward force due to the low pressure within vacuum chamber 40, ball 60 returns to its position blocking waste exit aperture 58 and sealed against O-ring 62. Of course, water continues to flow into drain chamber 46 from reservoir overflow tube 76 and then out drain tube 24. It should be noted that the position of bottom baffle 54 relative to bottom end cap 38 is critical. If the distance between bottom baffle 54 and bottom end cap 38 is too great, ball 60 can move radially beyond the limits of second recess 80 and ball 60 will not be lifted into place by the low pressure in vacuum chamber 40. If this occurs, ball 60 could become stuck or may not otherwise be able to return to its position to block waste exit aperture 58. Thus, ball 60 should only be able to move radially to the edges of second recess 80, but not beyond. If the distance between bottom baffle 54 and bottom end cap 38 is too small, ball 60 will not be able to move enough to allow fluid and particulates to drain properly.

After mixture 88 has passed through filter 68, into filtered chamber 42, and through vacuum line access port 20 to vacuum pump 12, the filtered liquid is exhausted, along with water used by vacuum pump 12 as a coolant and sealant, through exhaust line port 16. In the preferred embodiment, this water is used to create reservoir 86 within reservoir chamber 44. When vacuum pump 12 is first turned on, reservoir chamber 44 is substantially empty. The low pressure created in vacuum chamber 40 and in filtered chamber 42 causes ball 82 to be pulled downward along top baffle 50 to block reservoir exit aperture 84, and water begins to flow from exhaust line port 16, through exhaust line hose 30, and into reservoir chamber 44 via reservoir input port 22. As water begins to flow into reservoir chamber 44, it displaces air in reservoir chamber 44, which is vented through air vent 48. Air vent 48 allows self-purifying assembly 10 to comply with many local building codes that require that there be no positive pressure on a sewer line, such as is accessed by reservoir overflow tube 76, drain chamber 46, and drain tube 24. Airvent 48 can be easily capped if an air vent is not required. When the water level in reservoir chamber 44 reaches upper end 78 of reservoir overflow tube 76, water begins to flow through reservoir overflow tube 76 into drain chamber 46 and out drain tube 24.

Figure 3:
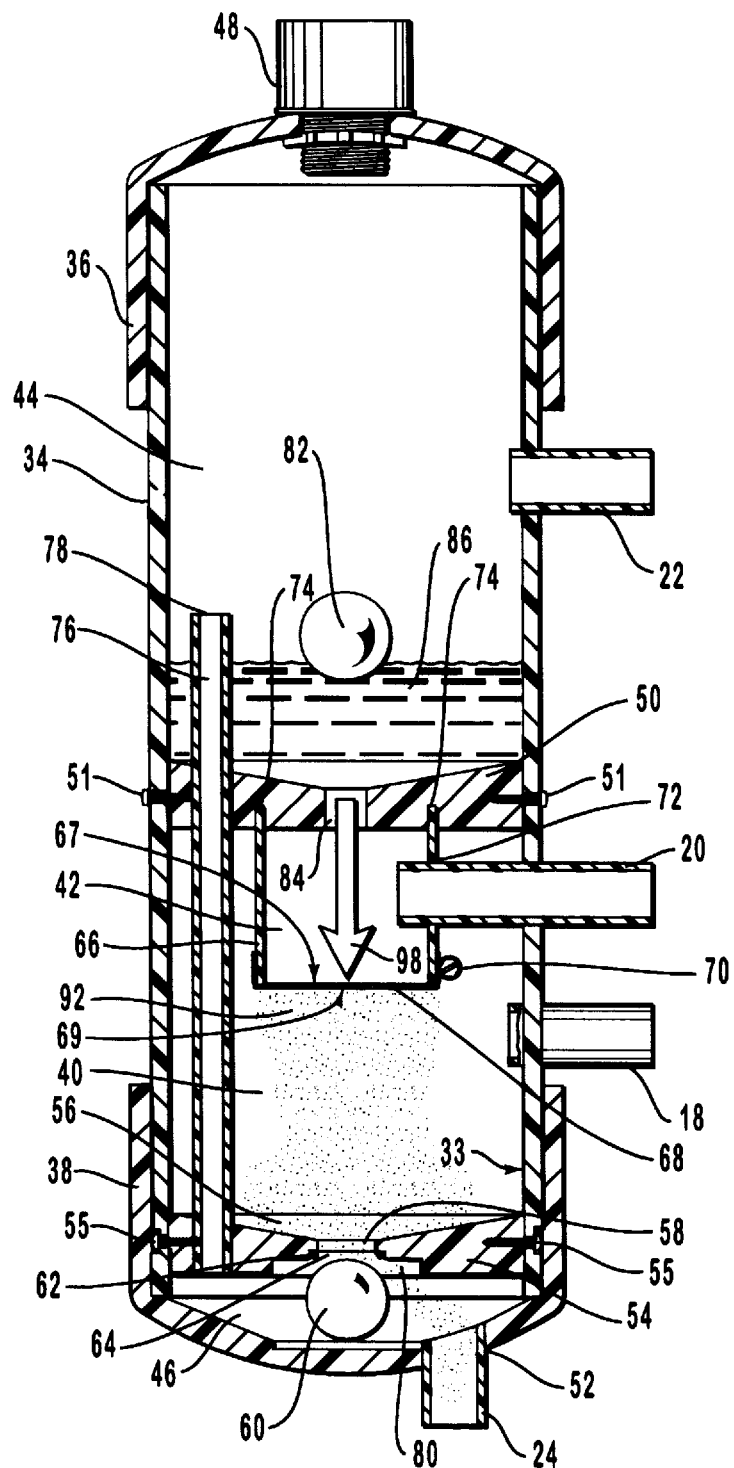
FIG. 3 is the same cross-sectional view of the self-purifying filter assembly as presented in FIG. 2, except that it reveals the path of flow of solid particulates and fluid while the reservoir in the self-purifying filter is operating to rinse from the filter solid particulates previously deposited thereon.

As illustrated in FIG. 3, when vacuum pump 12 is turned off, ball 82 is no longer pulled downward by virtue of the low pressure within vacuum chamber 40 and therefore, ball 82 floats upward through reservoir 86, allowing the water to flow as a stream 98 through reservoir exit aperture 84, into filtered chamber 42, and through filter 68 by passing from upper surface 67 to lower surface 69. Stream 98 causes deposits 92 on lower surface 69 of filter 68 to be removed, and the resulting mixture falls to top surface 56 of bottom baffle 54 and through waste exit aperture 58, which is no longer blocked by ball 60 because vacuum pump 12 has been turned off. Thus, the mixture of the water of stream 98 and deposits 92 flows into drain chamber 46 and out drain tube 24.

It should be noted that the diameter or size of reservoir exit aperture 84 is significant. If reservoir exit aperture 84 is too large, ball 82 will not float upwards through reservoir 86 when vacuum pump 12 is turned off. In addition, if reservoir exit aperture 84 is too small, ball 82 does not adequately seal reservoir exit aperture 84 while vacuum pump 12 is on.

It should be noted that reservoir 86, reservoir chamber 44, ball 82, and top baffle 84 form collectively only one purging means for causing a stream of liquid or fluid to flow back through filter 68. Many other means may be used. For example, an independent water source may be used to fill reservoir chamber 44, or the use of reservoir 86 could be replaced altogether by any stream of fluid from an independent source. Any other means that can cause a fluid to be passed through filter 68 can be used. Filter 68 could be rinsed while vacuum pump 12 is still in operation in some embodiments.

It should also be noted that, in connection with the use of reservoir chamber 44, a different valving system could be used. Ball 82 is just one means of allowing reservoir 86 to pass through reservoir exit aperture 84 and rinse filter 68. In other embodiments, a solenoid valve or many other types of commercially available valves could be used. Ball 82 of the preferred embodiment simply allows self-purifying assembly 10 to eliminate the need for additional electrical connections. Similarly, the use of reservoir chamber 44 and reservoir 86 allow self-purifying filter assembly 10 to eliminate the need for outside waterline hookups.

In addition, reservoir overflow tube 76 does not necessarily have to pass through vacuum chamber 40. It could be routed directly from reservoir chamber 44 through outer tube 34 to a sewer or through some other route to drain chamber 46. In addition, other valve means may be used besides ball 60. Solenoid valve or other commercially available valves could also be used to allow access from vacuum chamber 40 into drain chamber 46. Again, the use of ball 60 simply allows the preferred embodiment of self-purifying filter assembly 10 to require no electrical connections.

The invention may be embodied in other specific forms without departing from its spirit or essential characteristics. Consequently, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A self-purifying filter system comprising:
   (a) a vacuum chamber;
   (b) a filtered chamber having an aperture that allows access from said vacuum chamber into said filtered chamber, said aperture being covered by a filter, said filter having an inner surface inside said filtered chamber and an outer surface outside said filtered chamber;
   (c) flow control means for selectively causing a fluid to flow from said vacuum chamber to said filtered chamber; and
   (d) purging means for causing a stream of liquid to pass through said filter from said inner surface to said outer surface said purging means comprises a reservoir of liquid, a reservoir exit aperture, and a valve which comprises a ball that continuously covers said reservoir exit aperture while said flow control means is causing said fluid to flow but said ball floats upward in the liquid in said reservoir, thereby uncovering said reservoir exit aperture, when said flow control means stops causing the fluid to flow.

2. A self-purifying filter system as recited in claim 1, wherein said vacuum chamber and said filtered chamber are substantially cylindrical.

3. A self-purifying filter system as recited in claim 2, wherein said filtered chamber is disposed substantially concentrically within said vacuum chamber.

4. A self-purifying filter system as recited in claim 3, wherein said vacuum chamber and said filtered chamber each have a longitudinal axis that is oriented substantially vertically.

5. A self-purifying filter system as recited in claim 1, wherein said flow control means uses and exhausts liquid, and said reservoir comprises liquid that has been exhausted from said flow control means.

6. A self-purifying filter system comprising:
   (a) a vacuum chamber comprising:
      (i) a mixture inlet port,
      (ii) a waste exit aperture, and
      (iii) a valve, said waste exit aperture being blocked by said valve until a trigger event, whereby when a mixture of solid particulates and liquid enters said vacuum chamber via said mixture inlet port, at least some of said solid particulates accumulate in said vacuum chamber, and said valve blocks said accumulated solid particulates from passing through said waste exit aperture until said trigger event; and
   (b) a filtered chamber having an aperture that allows access from said vacuum chamber into said filtered chamber, said aperture being covered by a filter, said filter having an inner surface inside said filtered chamber and an outer surface outside said filtered chamber;
   (c) flow control means for selectively causing a fluid to flow from said vacuum chamber to said filtered chamber; and
   (d) purging means for causing a stream of liquid to pass through said filter from said inner surface to said outer surface said purging means comprises a reservoir of liquid, a reservoir exit aperture, and a valve which comprises a ball that continuously covers said reservoir exit aperture while said flow control means is causing the fluid to flow, but said ball floats upward in the liquid in said reservoir, thereby uncovering said reservoir exit aperture, when said flow control means stops causing the fluid to flow.

7. A self-purifying filter system as recited in claim 6, wherein said waste exit aperture valve comprises a ball that continuously covers said waste exit aperture until said trigger event, and wherein said trigger event includes when said flow control means stops causing said fluid to flow or when the mass of said accumulated solid particulates has reached a trigger value.

\* \* \* \* \*